(12) United States Patent
Bester, Jr. et al.

(10) Patent No.: US 8,353,886 B2
(45) Date of Patent: Jan. 15, 2013

(54) MALE HYGIENIC ARTICLE AND DISPENSER THEREFOR

(75) Inventors: Kenneth W. Bester, Jr., Appleton, WI (US); Joseph DiPalma, Neenah, WI (US); MaryAnn Zunker, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1031 days.

(21) Appl. No.: 11/300,824

(22) Filed: Dec. 15, 2005

(65) Prior Publication Data
US 2007/0142794 A1 Jun. 21, 2007

(51) Int. Cl.
*A61F 5/44* (2006.01)

(52) U.S. Cl. ........ 604/347; 604/327; 604/351; 604/396; 604/358; 604/365

(58) Field of Classification Search ............ 604/327, 604/351, 396, 349, 347, 358, 365; 602/73, 602/70, 79
See application file for complete search history.

(56) References Cited

U.S. PATENT DOCUMENTS

| | | | | |
|---|---|---|---|---|
| 3,097,644 A | * | 7/1963 | Parker | 602/79 |
| 3,186,404 A | * | 6/1965 | Gardner | 602/13 |
| 3,307,546 A | * | 3/1967 | Cherio et al. | 602/79 |
| 3,322,118 A | * | 5/1967 | Sotherlin | 128/892 |
| 3,661,156 A | | 5/1972 | McLaughlin | |
| 4,589,875 A | | 5/1986 | Stringer | |
| 4,668,229 A | | 5/1987 | Fago et al. | |
| 4,911,151 A | * | 3/1990 | Rankin et al. | 602/3 |
| 5,331,670 A | * | 7/1994 | Sorbara et al. | 375/362 |
| 5,558,659 A | * | 9/1996 | Sherrod et al. | 604/385.26 |
| 6,336,919 B1 | | 1/2002 | Davis et al. | |
| 6,487,728 B1 | | 12/2002 | Cook | |
| 6,580,011 B1 | | 6/2003 | Jennings-Spring | |
| 6,916,301 B1 | * | 7/2005 | Clare | 602/3 |
| 2001/0007934 A1 | | 7/2001 | Smith | |
| 2003/0050589 A1 | * | 3/2003 | McDevitt et al. | 602/41 |
| 2003/0119396 A1 | * | 6/2003 | Koenig et al. | 442/123 |
| 2004/0059308 A1 | | 3/2004 | Odderson | |

FOREIGN PATENT DOCUMENTS

| | | |
|---|---|---|
| DE | 19916283 A1 | 10/2000 |
| EP | 0 903 131 A1 | 3/1999 |
| WO | 2005044166 A1 | 5/2005 |

OTHER PUBLICATIONS

Healthwise, Condom Catheter, from webmd.com dated Nov. 14, 2005, 1 page.
International Search Report for PCT/US2006/038916, dated May 11, 2007, 4 pages.

* cited by examiner

*Primary Examiner* — Tatyana Zalukaeva
*Assistant Examiner* — Ilya Treyger
(74) *Attorney, Agent, or Firm* — Armstrong Teasdale LLP (57) ABSTRACT

A hygienic article for personal wear by a male includes an elongate fabric sleeve having a first end, a longitudinally opposite second end, and a central passage extending longitudinally between the first and second ends of the sleeve. The first end of the sleeve is open to the central passage to permit the wearer's penis to extend through the open first end into the central passage of the sleeve with the first end of the sleeve nearer to the base of the wearer's penis than the second end of the sleeve. The second end of the sleeve is also open to the central passage to permit the wearer to urinate through the open second end. A dispenser is adapted for holding a plurality of such hygienic articles and facilitating sequential dispensing of the hygienic articles, one at a time, from the dispenser.

13 Claims, 14 Drawing Sheets

MALE HYGIENIC ARTICLE AND DISPENSER THEREFOR

FIELD OF INVENTION

This invention relates generally to hygienic articles for personal wear by males to take in and retain body fluids away from the wearer's skin, and more particularly to such hygienic articles which are intended for wear on a male's penis to take in and retain residual fluids.

BACKGROUND

The skin of a male's penis may be exposed to various bodily fluids such as sweat, urine and semen that can lead to poor skin health and hygiene. For example, residual urine is sometimes left on the skin of the penis following urination, or may leak from the penis following urination or due to light incontinence. Such incidents are even more prevalent in atypical conditions such as hypospadias (where the urethra is open on the underside of the shaft of the penis) and epispadias (where the urethra is open on the upper side of the shaft of the penis).

One possible solution to guarding the skin of the penis against such residual fluid loss is to wear incontinence garments, which are absorbent garments (and more typically disposable absorbent garments) that resemble and are worn in the manner of conventional undergarments. However, incontinence garments are intended more for taking in and retaining a more substantial volume of fluid, such as where an entire urination event, or insult, occurs. Incontinence garments are rather bulky and therefore non-discrete, often presenting emotional and/or psychological obstacles to the wearing of such garments. Moreover, only certain portions of the wearer's penis would sufficiently contact the incontinence garment, meaning that residual fluids would still remain on other and potentially larger portions of the skin including the abdomen, buttocks, and groin. Female hygienic articles such as pantyliners or pads may also adequately function to some extent, but such articles are distinctively associated with women and would also present emotional and psychological obstacles for a male wearer.

There is a need for a discrete hygienic article for wearing on a male's penis to take-in and retain residual fluids released by the wearer while minimizing contact with adjacent body surfaces.

SUMMARY

In one aspect, the present invention is directed to a hygienic article for personal wear by a male. The hygienic article generally comprises an elongate fabric sleeve having a first end, a longitudinally opposite second end, and a central passage extending longitudinally between the first and second ends of the sleeve. The first end of the sleeve is open to permit the wearer's penis to extend through the open first end into the central passage of the sleeve with the first end of the sleeve nearer to the base of the wearer's penis than the second end of the sleeve. The second end of the sleeve also is open to permit the wearer to urinate through the open second end.

In another aspect, the present invention is directed to a hygienic article for personal wear by a male. The hygienic article generally comprises an elongate fabric sleeve having a first end, a longitudinally opposite second end, and a central passage extending longitudinally between the first and second ends of the sleeve. The first end of the sleeve is open to permit the wearer's penis to extend through the open first end into the central passage of the sleeve with the first end of the sleeve nearer to the base of the wearer's penis than the second end of the sleeve. The second end of the sleeve also is open. A closure is secured to the sleeve and selectively configurable between a closed position in which the closure substantially closes the second end of the sleeve and an open position in which the second end of the sleeve is free from being blocked by the closure to permit the wearer to urinate through the open second end of the sleeve.

In yet another aspect, the present invention is directed to a combination dispenser and plurality of hygienic articles for personal wear by a male. Each hygienic article comprises an elongate fabric sleeve having a first end, a longitudinally opposite second end, and a central passage extending longitudinally between the first and second ends of the sleeve. The dispenser is adapted for holding the plurality of hygienic articles and facilitating sequential dispensing the hygienic articles, one at a time, from the dispenser.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
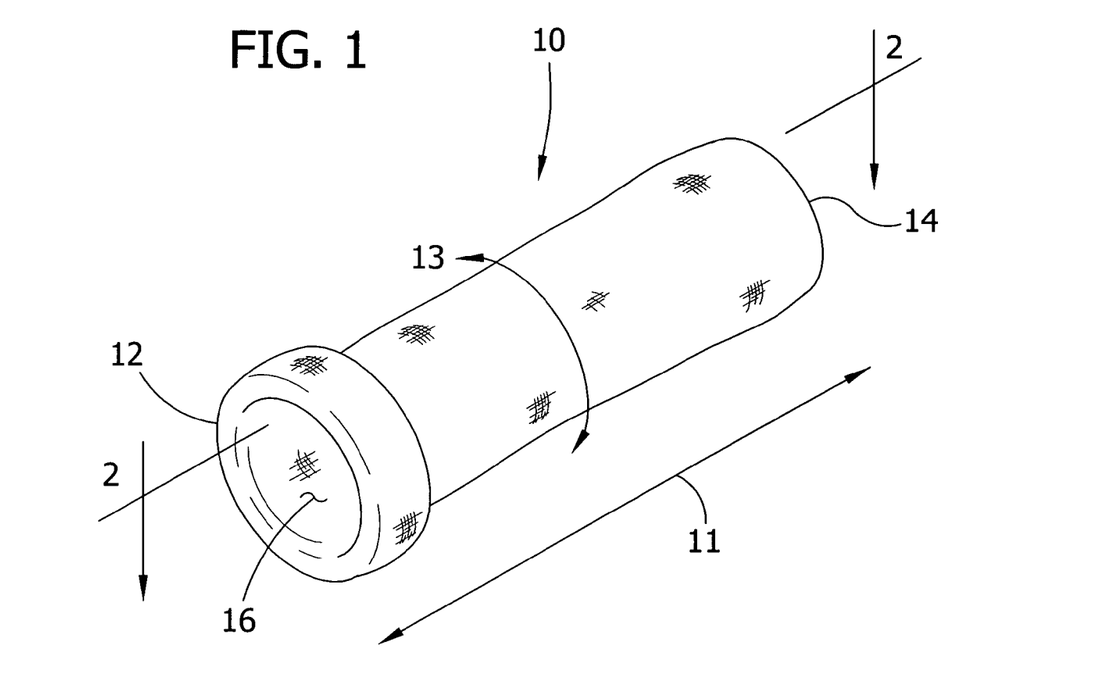
FIG. 1 is a perspective view of one embodiment of a hygienic article in the form of a sleeve for receiving a penis of a male wearer.
Figure 2:
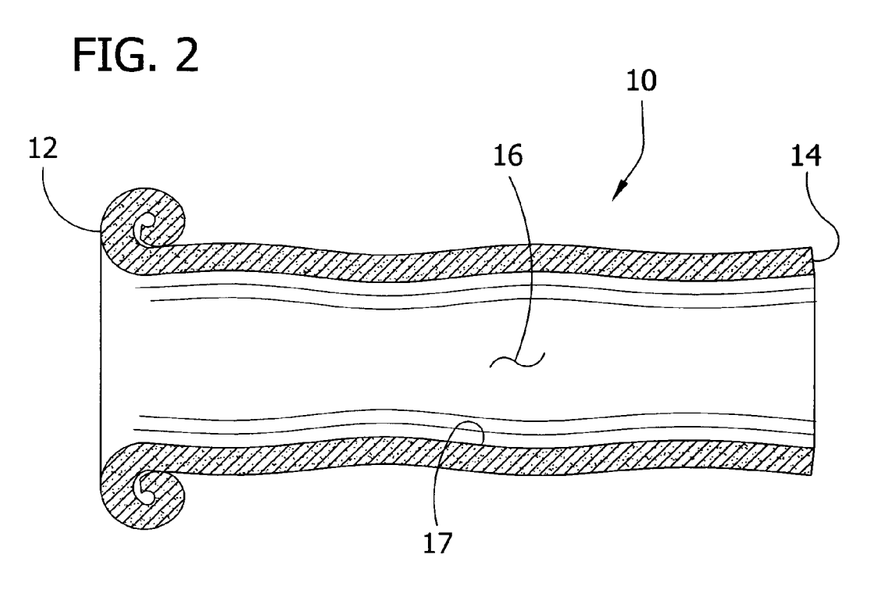
FIG. 2 a cross-section taken in the plane of line 2-2 of FIG. 1.

Referring now to the drawings and in particular to FIGS. 1-2, one embodiment of a hygienic article for personal wear by a male comprises an elongate fabric sleeve and is generally designated by reference numeral 10. The sleeve 10 is suitably sized and shaped for receiving at least a portion of the length of wearer's penis and is constructed to take-in and retain residual fluids (i.e., urine, semen, sweat, etc.) commonly associated with the penis.

The illustrated sleeve 10 has a first end 12, a longitudinally opposite second end 14, and a central passage 16 defined by an inner surface 17 (FIG. 2) extending longitudinally between the first and second ends of the sleeve. The sleeve 10 has a longitudinal direction 11 extending longitudinally between the first and second ends of the sleeve and a transverse direction 13 extending circumferentially about the sleeve. The first end 12 of the sleeve 10 is suitably open to the central passage of the sleeve to permit the wearer's penis to extend through the open first end into the central passage 16 of the sleeve with the first end of the sleeve positioned nearer to a base B (FIG. 3) of the wearer's penis than the second end 14 of the sleeve. The second end 14 of the sleeve 10 is also suitably open to the central passage 16 of the sleeve such that the sleeve does not block the flow of urine from the penis during a normal urination event. That is, the wearer does not have to urinate into or through the sleeve 10. Accordingly, a wearer may discretely wear the sleeve 10 while in a public restroom without having to remove the sleeve before or after urinating.

Figure 3:
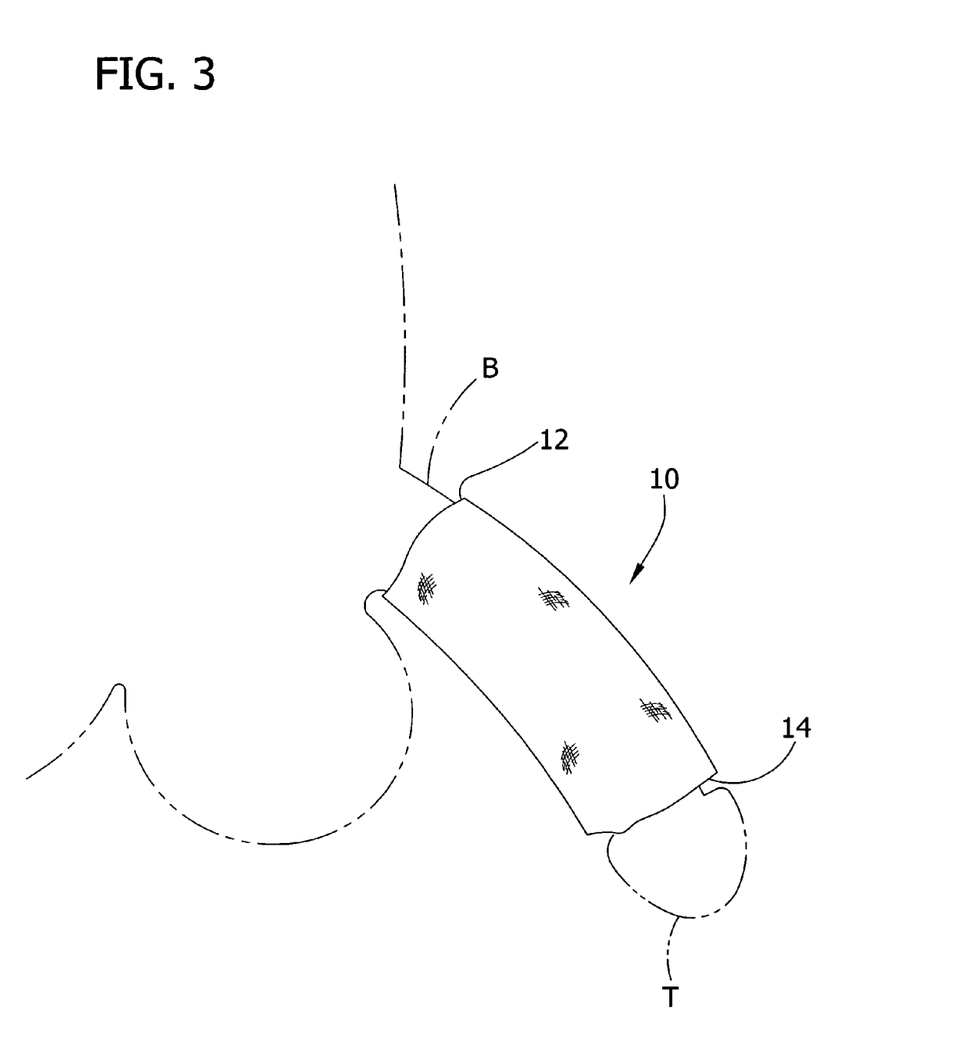
FIG. 3 is a side elevation showing the wearer's penis being received in the sleeve of FIG. 1.
Figure 4:
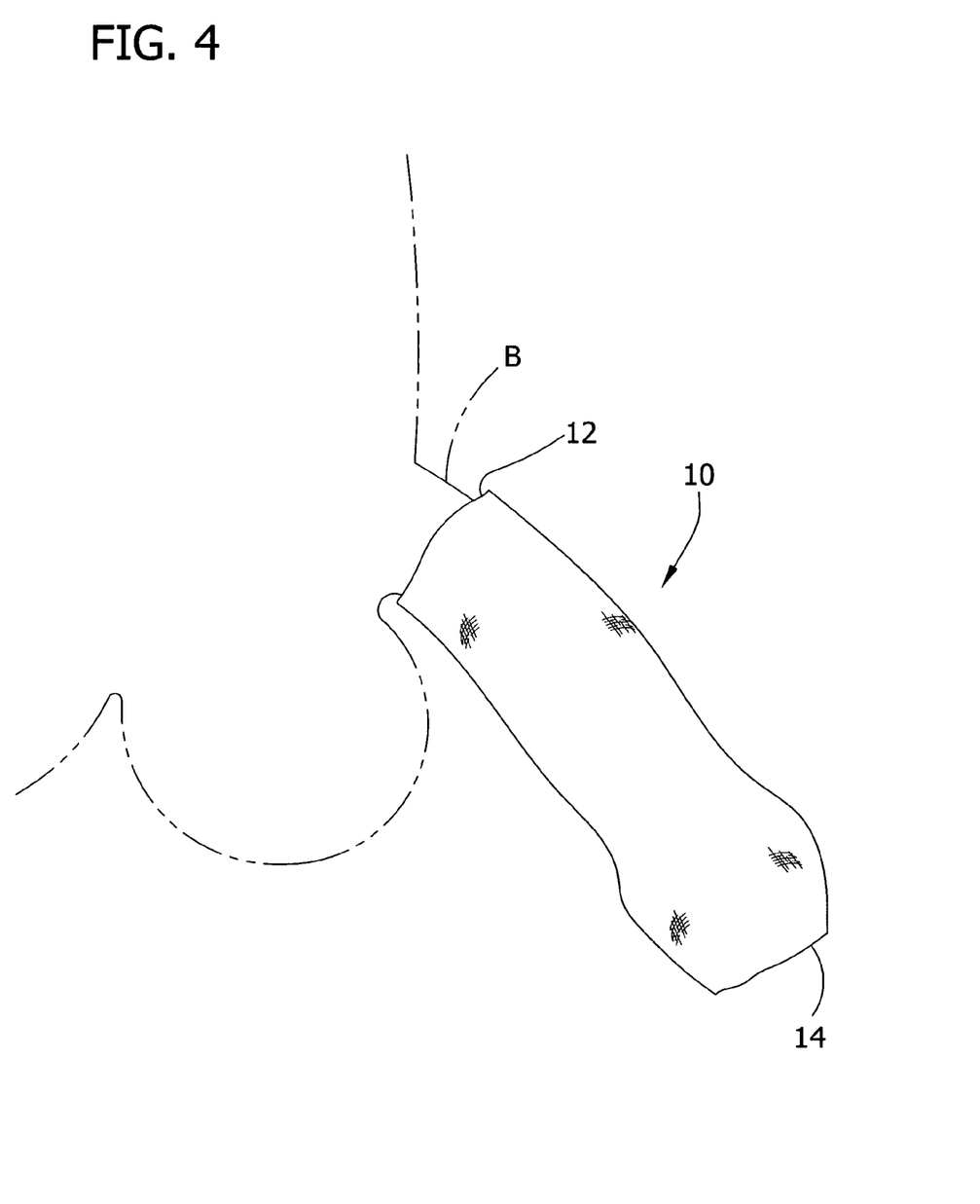
FIG. 4 is a side elevation similar to FIG. 3 but showing a tip of the wearer's penis covered by the sleeve.

In one suitable embodiment illustrated in FIG. 3, the sleeve 10 is suitably of a length such that the wearer's penis extends outward beyond the second end 14 of the sleeve during wear so that a tip T of the wearer's penis is uncovered by the sleeve 10. In an alternative embodiment as illustrated in FIG. 4 the length of the sleeve 10 is such that the second end 14 of the sleeve is disposed longitudinally outward beyond the tip T of the wearer's penis during wear. That is the sleeve 10 encircles the circumference of the wearer's penis at the tip T but is otherwise still open at the second end 14 to avoid having to urinate into and/or through the sleeve during a normal urination event.

Figure 6:
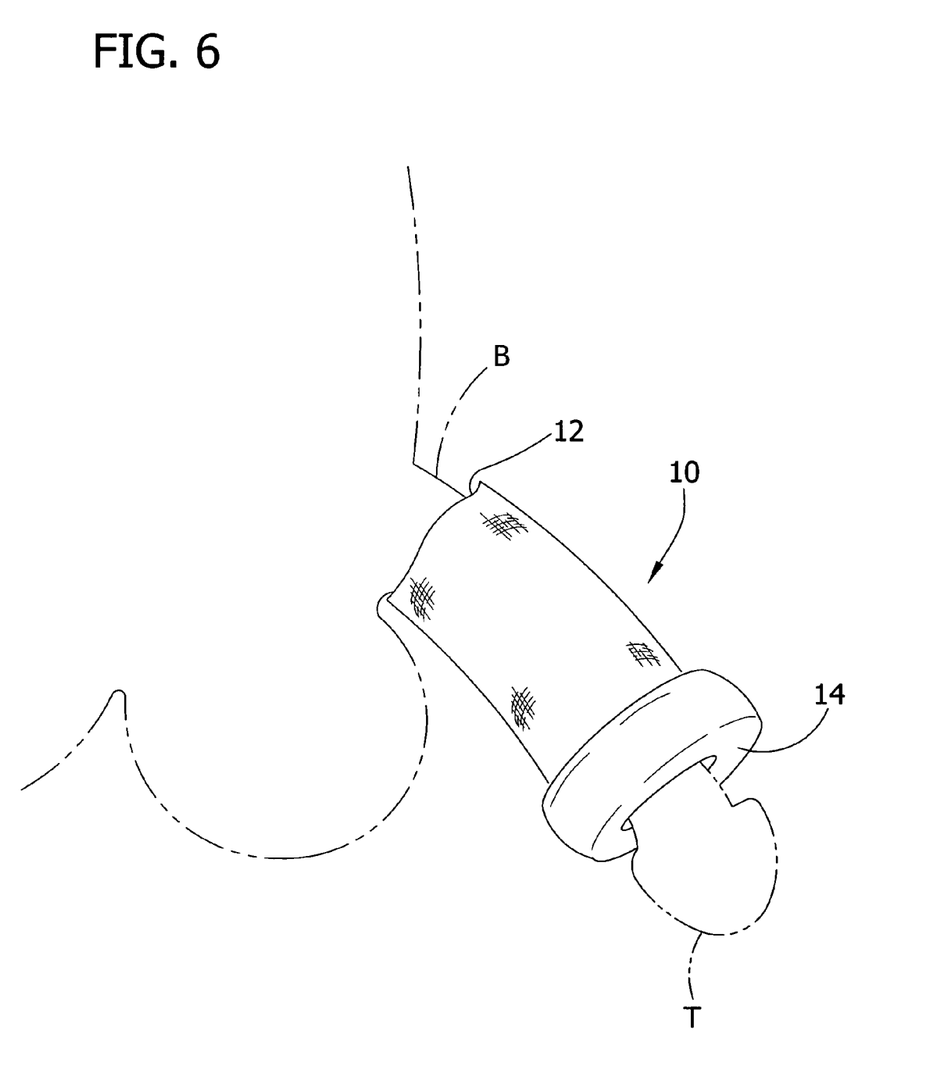
FIG. 6 is a side elevation similar to FIG. 5 but showing the closure in an open position in which the end of the sleeve is unblocked by the closure.

It is understood, though, that the sleeve 10 may be sized in length other than as illustrated in FIGS. 3 and 4 without departing from the scope of this invention. For example, the sleeve 10 may be sized for positioning of the first end 12 further away from the base B of the penis so that the sleeve covers only a portion of the shaft of the penis, with the second end 14 of the sleeve still being disposed respectively inward of, generally at or outward beyond the tip T of the wearer's penis The fabric from which the sleeve 10 is constructed may also be sufficiently flexible to permit the first end 12 of the sleeve to be folded or rolled up on itself (e.g., toward the second end 14 of the sleeve), and more suitably folded or rolled outward upon itself as illustrated in FIGS. 1 and 2 to selectively adjust the length of the sleeve. Alternatively, or additionally, the sleeve 10 may be folded or rolled up on itself at the second end 14 of the sleeve (e.g., toward the first end 12 of the sleeve) as illustrated in FIG. 6. Another way to adjust the length is to cut the sleeve 10 transversely using a pair of scissors (or other suitable cutting implement) to the desired length.

The term "fabric" as in reference to the material from which the sleeve is constructed is intended to include woven materials and knitted materials as well as to non-woven materials, which are fibrous webs or materials formed without the aid of a textile weaving or knitting process. Suitable materials from which the fabric may be formed include, without limitation, synthetic fibers (for example, polyester or polypropylene fibers), natural fibers (for example, wood or cotton fibers), and combinations of natural and synthetic fibers. The fabric may be composed of a substantially hydrophobic material, and the hydrophobic material can, optionally, be treated with a surfactant or otherwise processed to impart a desired level of wettability and hydrophilicity.

Suitable non-woven fibrous webs for use in constructing the sleeve 10 may be formed by any known technique for forming non-woven fibrous webs including, without limitation, carding, air forming, air laying, wet laying, co-forming and the like. Suitable fibers may be meltblown fibers, spunbond fibers or other suitably formed fibers. Meltblown fibers may be formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface.

Spunbond fibers may be formed by extruding molten thermoplastic material as filaments from a plurality of fine capillaries of a spinnerette having a circular or other configuration, with the diameter of the extruded filaments then being rapidly reduced by a conventional process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, more particularly, between about 0.6 and about 10.

It is also contemplated that the fibers used in forming a suitable non-woven web for the sleeve 10 may be multicomponent fibers (e.g., bicomponent fibers) in which two or more components are used in forming each fiber, such as in a sheath-core arrangement, island-in-a-sea arrangement or other suitable arrangement.

Other suitable fabrics, and more suitably non-woven materials, for use in making the sleeve 10 may be formed at least in part of a biodegradable aliphatic polyester. The term biodegradable refers to the ability of a material to degrade due to the action of naturally occurring microorganisms such as bacteria, fungi, and algae. Various biodegradable aliphatic polyesters from which the non-woven web may be formed include, for example, polyesteramides, modified polyethylene terephtalate, polylactic acid (PLA), terpolymers based on polylactic acid, polyglycolic acid, polyalkylene carbonates (such as polyethylene carbonate), polyhydroxyalkanoates (PHA), polyhydroxybutyrates (PHB), polyhydroxyvalerates (PHV), polyhydroxybutyrate-hydroxyvalerate copolymers (PHBV), combinations thereof, and the like.

In one particularly suitable embodiment the sleeve may be a non-woven fabric of coform material. The term "coform material" generally refers to composite materials comprising a mixture or stabilized matrix of thermoplastic fibers and a second non-thermoplastic material. As an example, coform materials are made by a process in which at least one meltblown fiber die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. Nos. 4,100,324 to Anderson, et al.; 5,284,703 to Everhart, et al.; and 5,350,624 to Georger, et al.; which are incorporated herein by reference.

It is also understood that the sleeve 10 may be formed from two or more layers of any of the above materials or other suitable materials and remain within the scope of this invention, as long as the sleeve 10 is sufficiently constructed to take-in and retain residual fluids from the skin of the wearer's penis.

In another embodiment, the fabric sleeve 10 is suitably stretchable, and more suitably elastic, in at least of the transverse direction 13 and longitudinal direction 11 of the sleeve. Allowing the sleeve 10 to stretch in the transverse direction 13 provides the sleeve with the ability to conform to the penis of the wearer and provide a snug, comfortable fit. Longitudinal stretchability allows the sleeve 10 to conform to the length of the penis through various sizes (i.e., states of arousal) and positions of the penis. Accordingly, the sleeve 10 is inhibited against inadvertent shedding from the wearer's penis during prolonged use.

As used herein, the term "stretchable" refers to a material that may be extensible or elastomeric. That is, the material may be extended, deformed or the like, without breaking, and may or may not significantly retract after removal of an extending force. The term "elastic" refers to that property of a material where upon removal of an elongating force, the material is capable of recovering to substantially its unstretched size and shape or the material exhibits a significant retractive force. The term "extensible" refers to that property of a material where upon removal of an elongating force, the material experiences a substantially permanent deformation or the material does not exhibit a significant retractive force.

In particular, elastic materials utilized in connection with the fabric sleeve 10 may be elongated/extended or stretched in at least one direction without breaking by at least 25% (to at least 125% of its initial unstretched length) in at least one direction, suitably by at least 50% (to at least 150% of its initial unstretched length) and which will recover, upon release of the applied stretching or biasing force, at least 10% of their elongation. It is generally suitable that the elastic material or composite be capable of being elongated by at least 100%, more suitably by at least 200%, of its relaxed length and recover at least 30% and more suitably 50% of its elongation upon release of a stretching, biasing force, within about one minute.

Similarly, extensible or elongatable materials for use in making the sleeve 10 may be capable of stretching in at least one direction without breaking by at least 25% (to at least 125% of its initial unstretched length) in at least one direction, suitably by at least 50% (to at least 150% of its initial unstretched length), more suitably by at least 100% (to at least 200% of its initial unstretched length). As an example, an extensible material having an initial unstretched length of 3 inches (7.6 centimeters) may be stretched without breaking to a stretched length of at least 3.75 inches (9.5 centimeters) in at least one direction (for the "by at least 25%" value).

In one particularly suitable embodiment the sleeve 10 may comprise a three ply laminate such as a Stretch Bonded Laminate (SBL) that consists of two nonwoven facings attached to an elastic inner layer while the inner layer is in a stretched condition. One such suitable SBL material is disclosed in U.S. Pat. No. 4,657,802 to Morman, the disclosure of which is incorporated by reference herein. In another particularly suitable embodiment the sleeve 10 may comprise a Necked Bonded Laminate (NBL) that is also a three-ply laminate but the elastic inner layer is not pre-stretched prior to attaching the two nonwoven facings. For the NBL, the nonwoven facings are neck stretched and the elastic inner layer is attached between the necked facings. Other suitable elastically stretchable NBL materials as are described in U.S. Pat. No. 5,226,992 issued on Jul. 13, 1993 to Morman, the disclosure of which is hereby incorporated by reference.

In other suitable embodiments, the sleeve may comprise a non-woven web constructed from elastomeric materials that are treated using nonwoven manufacturing processes such as meltblowing. Suitable elastomers that may be formed into microfibers for making an elastic nonwoven web are described in U.S. Pat. No. 4,663,220 issued to Wisneski et al. on May 5, 1987 and titled "Polyolefin-Containing Extrudable Compositions and Methods for Their Formulation Into Elastomeric Products Including Microfibers", the disclosure of which is hereby incorporated by reference. Meltblowing of KRATON copolymers ("KRATON" is a trade designation of the Shell Chemical Company) to form composite nonwoven elastic webs is described in U.S. Pat. No. 4,657,802 issued to Morman on Apr. 14, 1987 and titled "Composite Nonwoven Elastic Web", the disclosure of which is hereby incorporated by reference.

In yet another particularly suitable embodiment, the sleeve 10 comprises an elastomeric coform material. Such materials are described for instance in U.S. Pat. Nos. 6,231,557 B1 and 6,362,389 B1, which are each incorporated by reference herein. Other examples of suitable elastomeric absorbent fabrics are described in international patent application WO 03/051254 and U.S. Pat. Nos. 5,964,743, 5,645,542, 6,231,557, and 6,362,389 B1, each of which are also incorporated by reference herein.

The sleeve 10 may have a suitable lubricious feature on its inner surface 17, such as by coating the inner surface with a lubricious element, by coating the individual fibers of the fabric sleeve with a lubricant, by impregnating the sleeve with such a lubricant or by other suitable applications. The lubricant is intended to facilitate sliding of the sleeve, first end 12 first, onto the wearer's penis without causing damage or irritation thereto. Examples of suitable lubricants include, without limitation, silicones, cyclomethicones, dimethicones, dimethiconol, PEG dimethicone, alkyl silicones, phenyl silicones, silicone phospholipids, silicone gums, silicone oils, silicone waxes, cyclopentasiloxane, dimethicone crosspolymers, and combinations thereof. Particular lubricants suitable for use on the sleeve 10 include, for example, Dow Corning® 9041 Silicone Elastomer Blend Dimethicone (and) Crosspolymer, Dow Corning® 9011 Silicone Elastomer Blend, Dow Corning® 9040 Silicone Elastomer Blend— Cyclomethicone (and) Dimethicone Crosspolymer, Dow Corning® 9045 Silicone Elastomer Blend Cyclopentasiloxane (and) Dimethicone Crosspolymer, Dow Corning® 9509 Silicone Elastomer Suspension Dimethicone/Vinyl Dimethicone Crosspolymer (and) C12-14 Pareth-12, Dow Corning® 2503 Cosmetic Wax (Stearyl Dimethicone) Alkyl Methyl Siloxanes, Dow Corning® 556 Cosmetic Grade Fluid (polyphenylmethylsiloxane), Dow Corning® 929 Cationic Emulsion Amodimethicone (and) Tallowtrimonium Chloride (and) Nonoxynol-10, Dow Corning® HMW 2220 Non-ionic Emulsion Divinyldimethicone/Dimethicone Copolymer (and) C12-C13 Pareth-3 (and) C12-C13 Pareth-23, Dow Corning® 2-8177 Emulsion Amodimethicone (and) C12-

C14 Sec-Pareth-7 (and) C12-C14 Sec-Pareth-5, all of which are available from Dow Corning of Midland, Mich., U.S.A. It is understood that other types of lubricants could also be used to lower the dynamic coefficients of friction of the inner surface 17 of the sleeve 10 with respect to the skin of the wearer. It is also envisioned that the sleeve 10, or at least the portion of the sleeve, can be made of a low friction material. In that case, the sleeve material would be considered the "lubricious feature". The lubricant may also include a bacteriostatic, antifungal, or other suitable genito-urinary compatible treatment.

Figure 5:
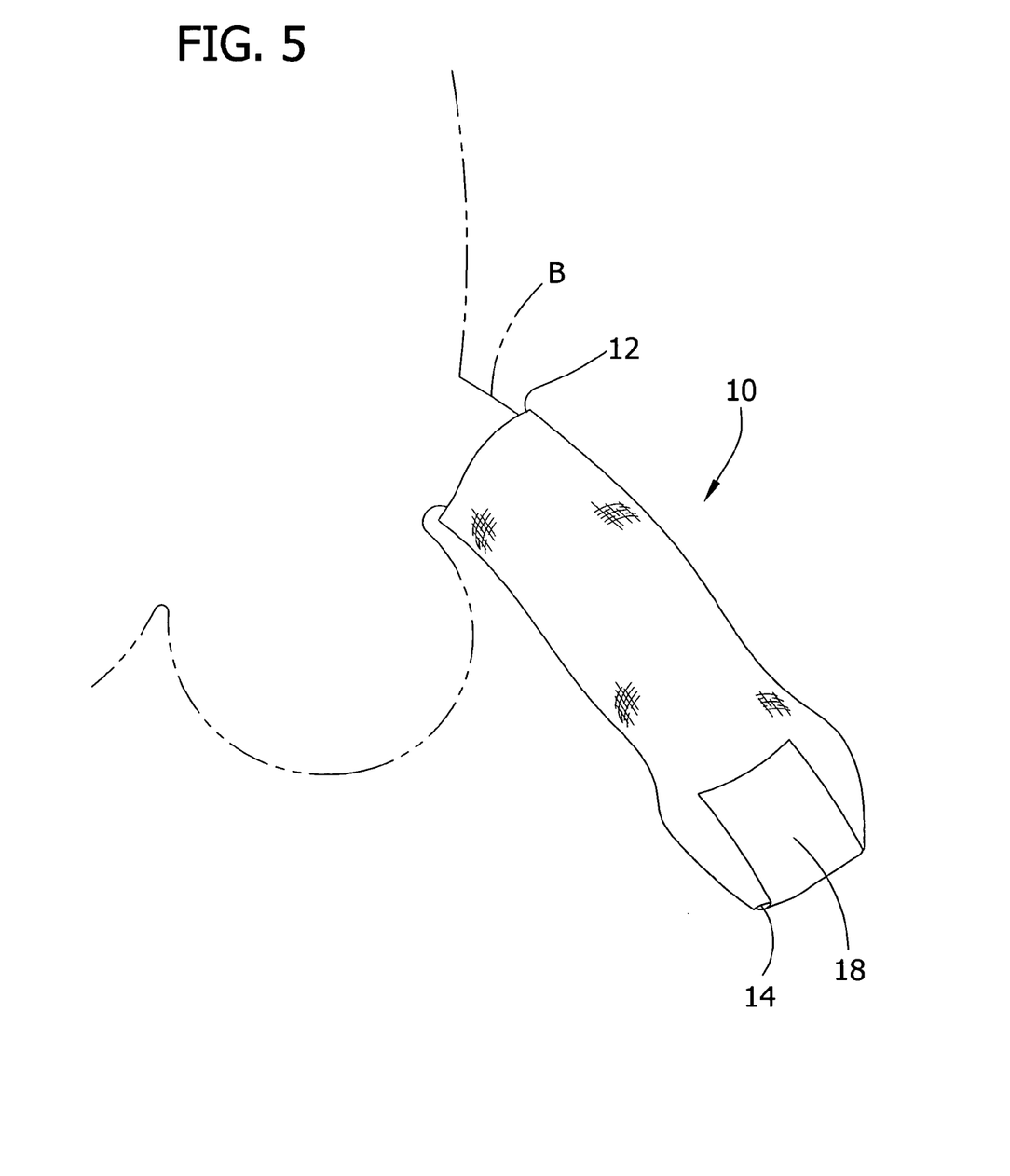
FIG. 5 is a side elevation of another embodiment of the sleeve having a closure in a closed position for closing a second end of the sleeve.

In another embodiment, illustrated in FIG. 5, a closure 18 is suitably provided for the second end 14 of the sleeve 10 to configure the sleeve in a closed position as illustrated in FIG. 5 in which the closure substantially closes the second end 14 of the sleeve 10 (FIG. 5). The closure is suitably removably disposed over the second end 14 of the sleeve to allow the sleeve to be selectively configured in an open configuration (FIG. 4) in which the wearer may urinate through the open second end of the sleeve, and then be reconfigured back to the closed configuration for a better enclosure around the tip T of the wearer's penis.

The illustrated closure 18 comprises a suitable strip of adhesive tape (broadly, a "fastening member") secured to the sleeve 10 adjacent the second end 14 of the sleeve with the sleeve generally pinched closed at the second end. The adhesive tape is selectively removable from (and refastenable to) the sleeve to permit configuring of the sleeve between its closed and open configuration. Alternatively, the second end 14 of the sleeve may be folded over to close the second end and held in this closed configuration by the adhesive tape 18. It is understood that other types of fastening members, such as hook and loop fasteners, buttons, pins, cohesives, mushroom-and-loop fasteners, or the like, can instead, or additionally, be used without departing from the scope of the invention. It also understood that the closure 18 may comprise a flap (not shown) or other component secured to or formed integrally with the sleeve 10 adjacent the second end 14 of sleeve and configured for selectively removably closing the second end of the sleeve.

The closure 18 may be suitably provided already secured to the sleeve 10, or it may be provided separately therefrom, such as on a roll of adhesive tape. Providing the closure 18 separate from the sleeve 10 gives the wearer more sleeve configuration options. Thus, the wearer has more options in altering the sleeve 10 to meet his preferences. Moreover, the sleeve can be made available to the wearer either individual or in bulk (i.e., more than one sleeve being package together).

Figure 7:
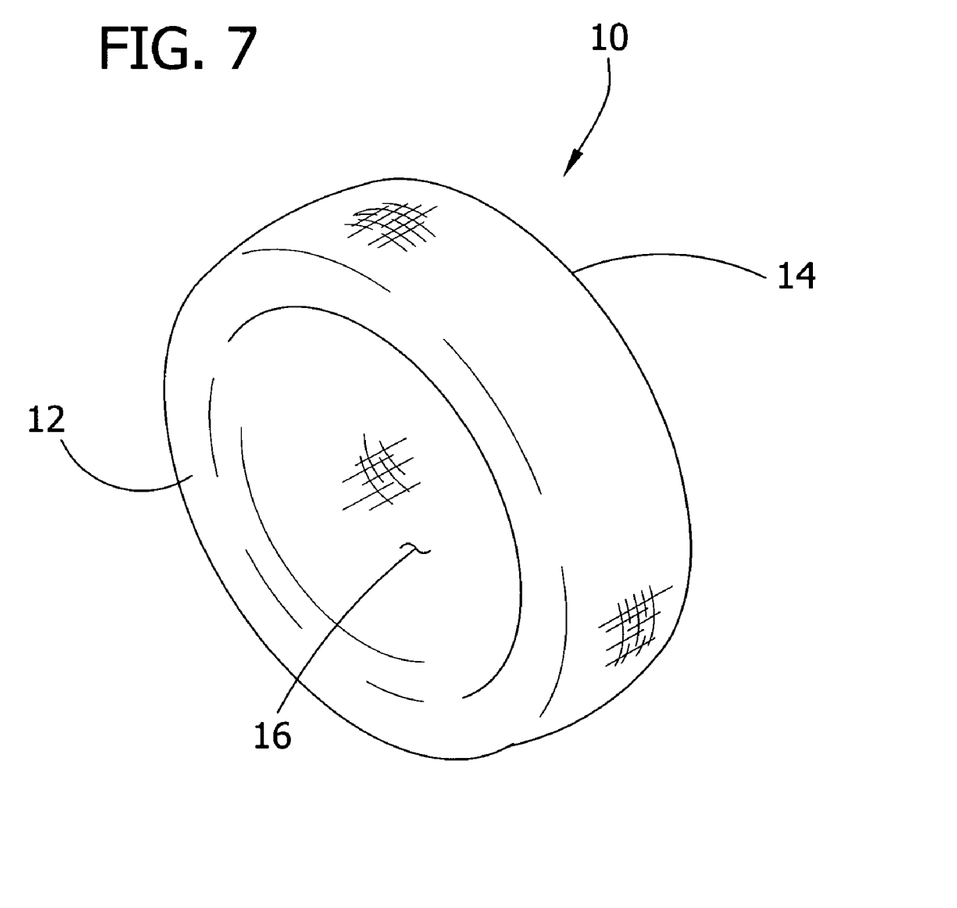
FIG. 7 is a perspective view a sleeve shown in FIG. 1 rolled longitudinally.
Figure 8:
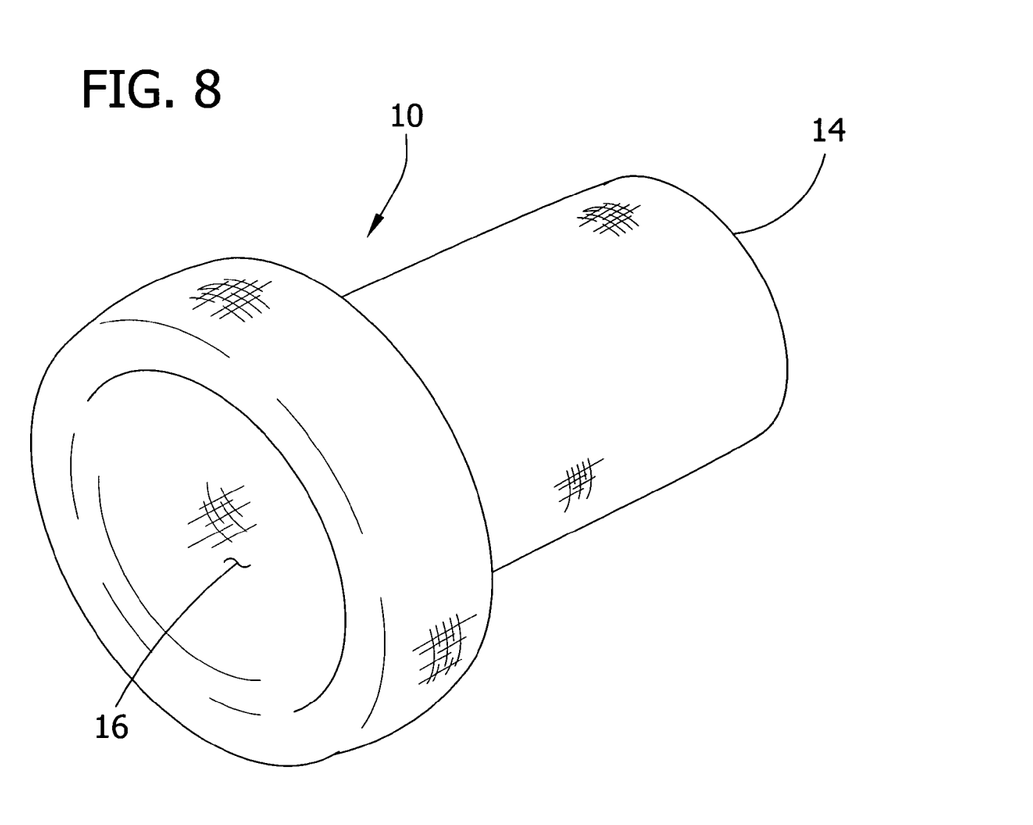
FIG. 8 is a perspective view similar to FIG. 7 but showing the sleeve partially unrolled.

As illustrated in FIGS. 7 and 8, the sleeve 10 can be provided to wearer in a completely rolled configuration in which the sleeve is rolled longitudinally upon itself (i.e., in the same manner as a condom). To use the sleeve 10, the wearer unrolls the sleeve 10 as illustrated in FIG. 8 to the wearer's desired length of the sleeve.

Figure 9:
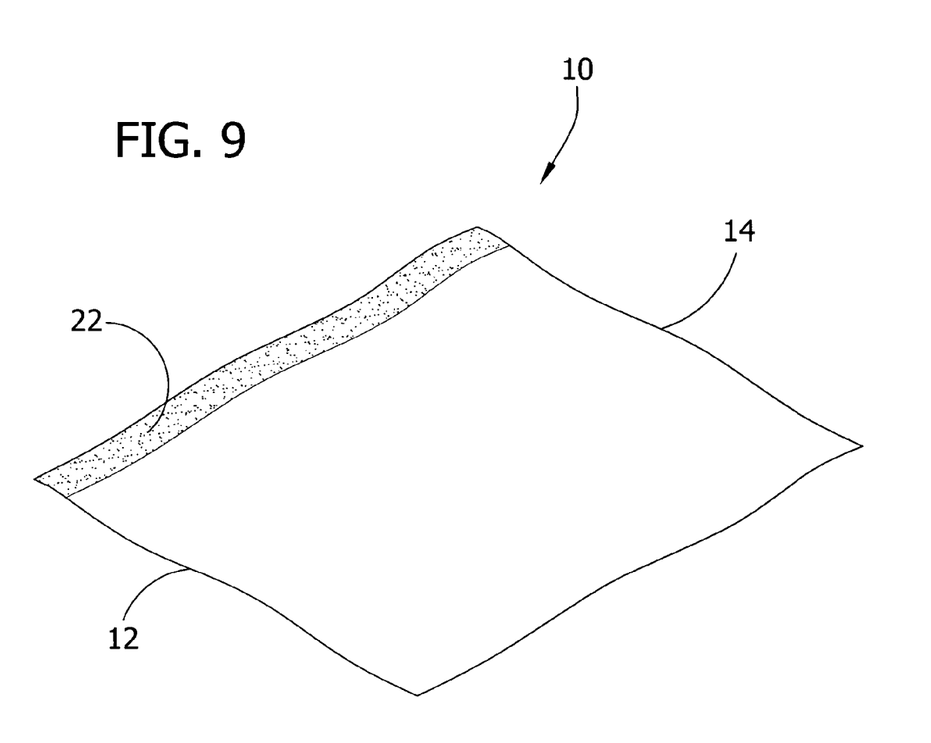
FIG. 9 is a perspective view of yet another embodiment of a sleeve in the form of a sheet adapted to wrap around a penis of a male wearer.
Figure 10:
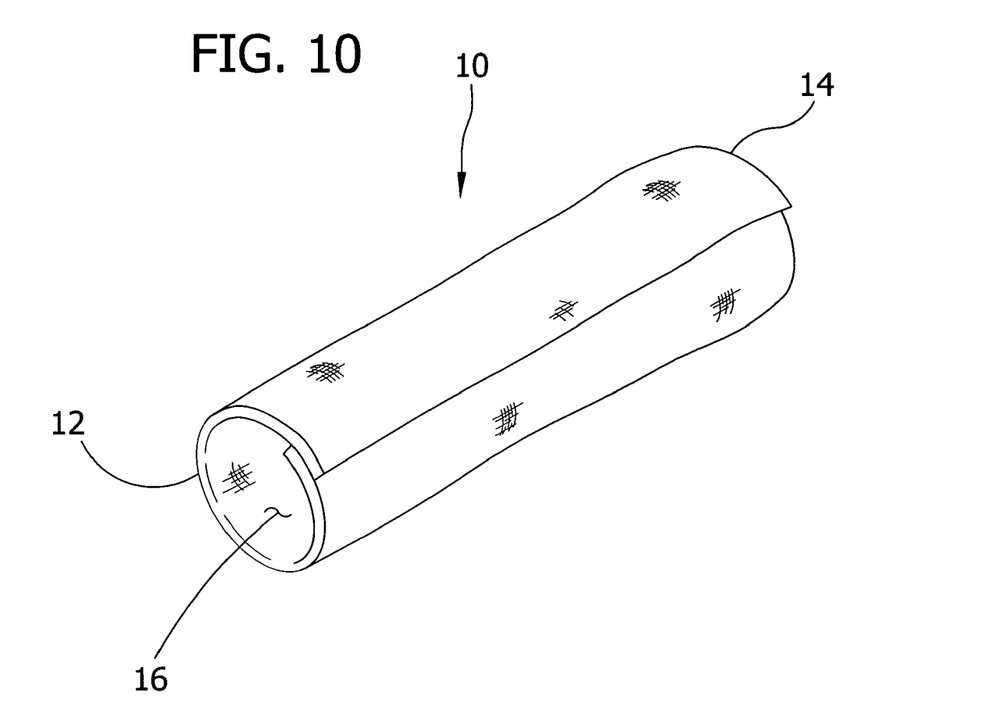
FIG. 10 is a perspective view of the embodiment shown in FIG. 9 showing the sheet wrapped as tube.

FIG. 9 illustrates another embodiment in which the sleeve 10 may be provided to the wearer in a sheet configuration (FIG. 9). In this configuration, the sleeve 10 is initially in the form of an unfolded or unrolled sheet. The sheet can be suitably configured in a tubular configuration (FIG. 10) defining the sleeve 10 by rolling the sheet transversely until portions of the sheet overlap along a longitudinal seam line. The sheet may have a suitable fastening member or members, such as adhesive 22 to secure the overlapped edges together. The sleeve 10 may rolled into its tubular configuration either before the wearer places it onto the penis, or more suitably it may be wrapped around the wearer's penis into the tubular configuration of the sleeve to provide a desired fit around the wearer's penis.

In packaging and dispensing a plurality of sleeves 10 in their sheet configuration, in one embodiment the plurality of sheets may be stacked, such as in the manner of tissues or wipes, and stored in a dispenser for subsequent dispensing, one sheet at a time. In another embodiment, a web of sleeves 10, each in sheet form (i.e., a web of sheets) may be formed and rolled (e.g., in the manner of toilet paper) for storage in a package or dispenser. The web may include lines of weakness, such as perforations or other material features that facilitate tearing of the web along the lines of weakness, to facilitate sequential separation of individual sheets from the roll. Alternatively, the web may be free of any lines of weakness or other delineating features that distinguish one sheet from the next. Such a configuration allows the wearer to sequentially cut each sheet to a desired length.

Figure 11:
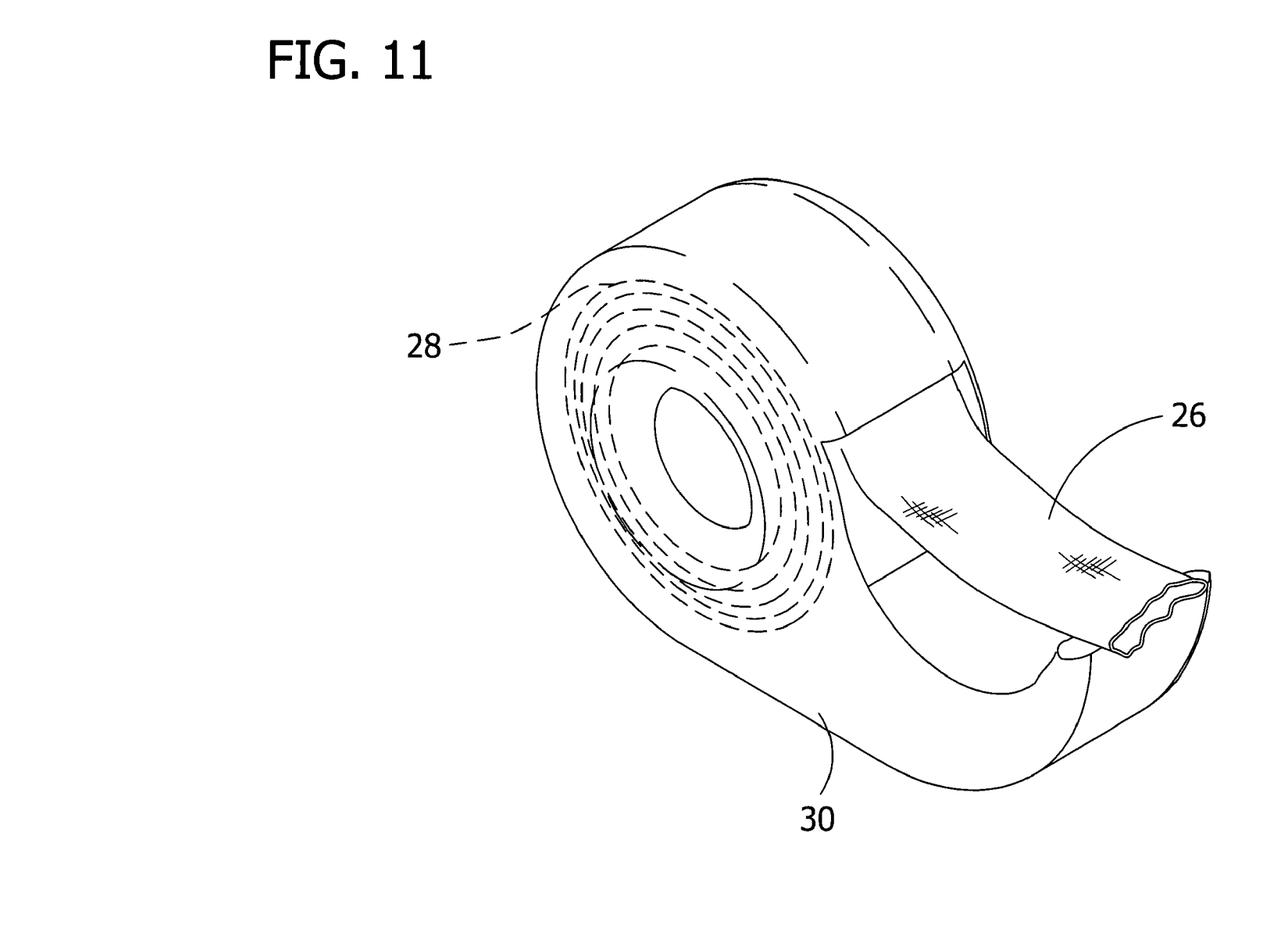
FIG. 11 is a perspective view of a continuous web of sleeve material coiled and received in a sleeve dispenser.
Figure 12:
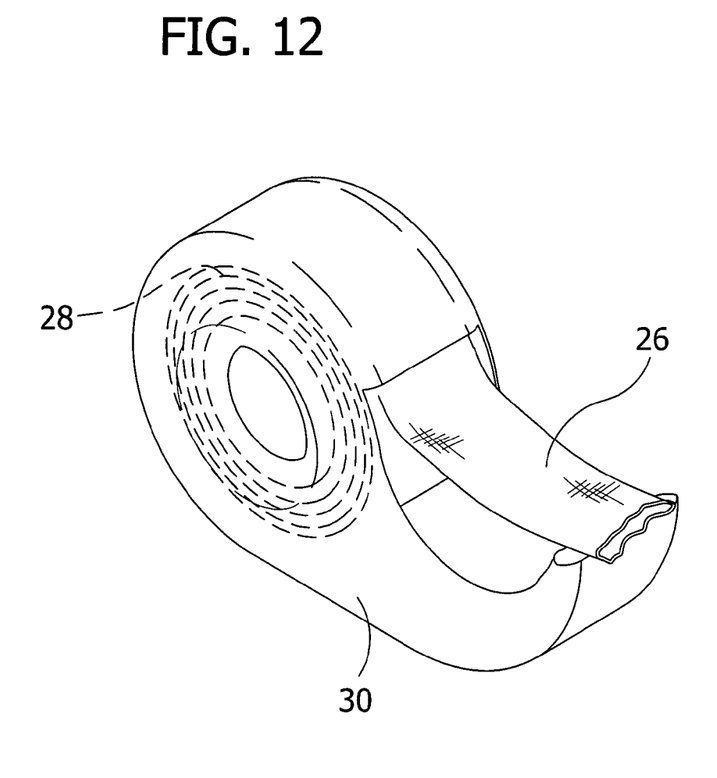
FIG. 12 is a perspective view of the dispenser showing a sleeve cut from the web.

In the alternative embodiment of FIGS. 11 and 12, a continuous web 26 of sleeves, already in a tubular configuration, is wound to form a roll or coil 28. In this arrangement, the wearer uncoils the web to a desired sleeve length and cuts or tears the web to form a discrete sleeve 10. Alternatively, the web may comprise lines of perforations to delineate one sleeve from the next and to facilitate sequential separation of one sleeve from the coil 28 at each line of weakness.

A suitable dispenser 30 may also be provided with the coil 28 for holding the coiled web of sleeves 10 and facilitating sequential dispensing of the sleeves 10, one at a time, from the dispenser. The coiled web 28 is mounted on the dispenser 30, such as in the manner of a tape dispenser, so that the coil may rotate to allow the web to be uncoiled. A blade (not shown) can be affix on the dispenser 30 for cutting the web of sleeve fabric. Alternatively, the dispenser may simply provide an edge against which the web is pulled to separate one sleeve 10 from the web along a line of weakness where such lines of weakness are provided. It is understood that the sleeve 10 may be dispensed in other suitable ways without departing from the scope of this invention.

Figure 13:
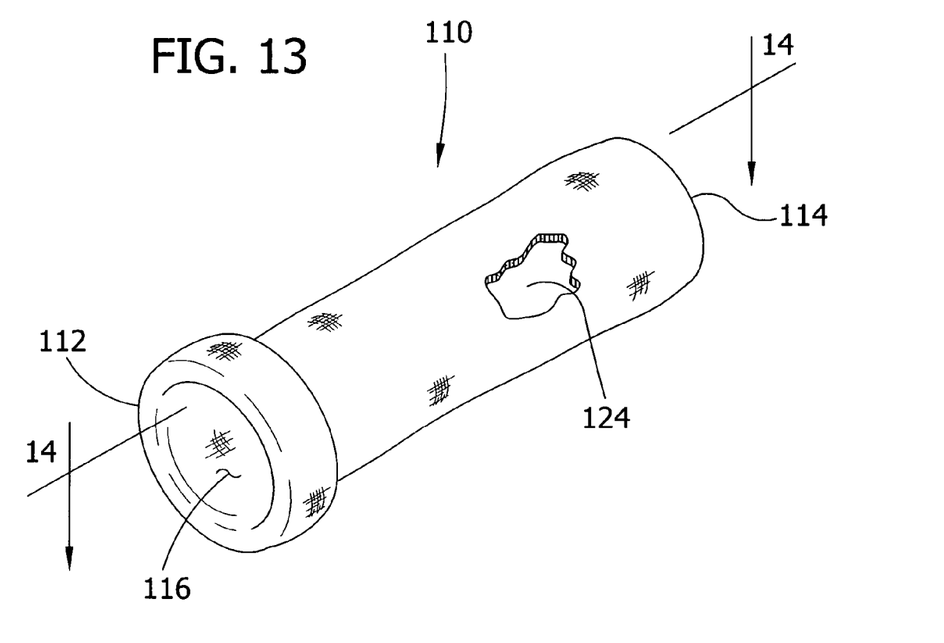
FIG. 13 is a perspective view of a sleeve of yet another configuration having a liner.
Figure 14:
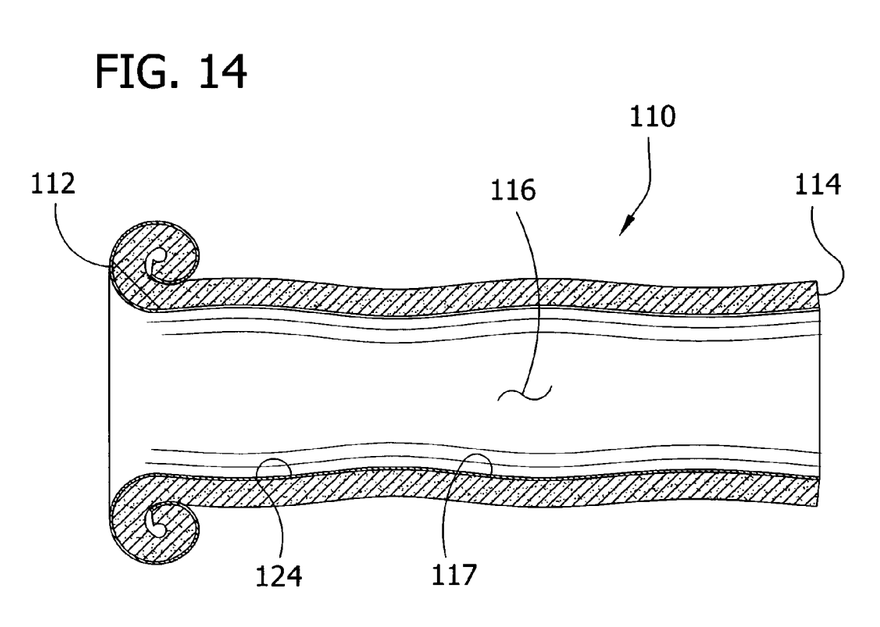
FIG. 14 is a cross-section taken in the plane of line 14-14 of FIG. 13.

FIGS. 13 and 14 illustrate another embodiment of a hygienic article also in the form of a sleeve 110. The sleeve has a liner 124 in the form of a wet wipe for lining at least a portion of the inner surface 117 of the sleeve within the central passage 116. Liners 124 suitable for use in lining the inner surface 117 of the sleeve 110 may be made from various materials and fibers, and are desirably soft to the touch. The liner 124 may be dry or wet to the touch. The liner 124 may be made from pulp fibers, other natural fibers, cellulose fibers, synthetic fibers such as polypropylene or polylactic acid, and the like. The liner 124 may be woven, knitted or nonwoven and may be sized to line the entire sleeve 110 or only a portion thereof. Moreover, the liner 124 may be elastic or inelastic.

One suitable liner 124 comprises a coform basesheet of polymeric microfibers and cellulosic fibers. Such coform basesheets are manufactured generally as described in U.S. Pat. No. 4,100,324, which is incorporated by reference. Typically, such coform basesheets comprise a gas-formed matrix of thermoplastic polymeric meltblown microfibers, such as, for example, polypropylene microfibers, and cellulosic fibers, such as, for example, wood pulp fibers. The relative percentages of the polymeric microfibers and cellulosic fibers in the coform basesheet can vary over a wide range depending upon the desired characteristics of the liner.

Alternatively, the liner 124 may comprise a composite, which includes multiple layers of materials such as those described in U.S. Pat. No. 6,028,018, which is incorporated by reference. For example, the liner 124 may be a three layer composite, which includes an elastomeric film or meltblown layer between two coform layers as described above.

As mentioned above and illustrated in FIGS. 13 and 14, the liner 124 may suitably be a wet wipe 124, which, in addition to the coform basesheet comprises a liquid solution or formulation. The liquid solution or formulation can be any liquid, which can be absorbed into the basesheet and may include any suitable components, which provide the desired wiping properties. For example, the components may include water, emollients, surfactants, fragrances, preservatives, chelating agents, pH buffers, or combinations thereof as are well known to those skilled in the art. Further, the liquid may also contain lotions, medicaments, lubricants, and/or antimicrobials. The sleeve 110 having the wet wipe liner 124 is well suited for use by the wearer for cleaning the penis.

The liner 124 may be secured to sleeve upon initial manufacture of the sleeve, or it may be assembled with the sleeve just prior to wear. For example, a wearer may wish to add the liner 124 to the sleeve 110 for cleaning the penis but may prefer to use an unlined sleeve when wearing the sleeve for an extended period of time.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above products without departing from the scope of the invention, it is intended that all matter contained in the above description and shown in the accompanying drawings shall be interpreted as illustrative and not in a limiting sense.

What is claimed is:

1. A hygienic article for personal wear by a male, said hygienic article comprising an elongate fabric sleeve having a first end, a longitudinally opposite second end and a central passage extending longitudinally between the first and second ends of the sleeve, the first end of the sleeve being open to the central passage to permit the wearer's penis to extend through said open first end into the central passage of the sleeve with the first end of the sleeve nearer to the base of the wearer's penis than the second end of the sleeve, the sleeve having an inner surface defining the central passage of the sleeve, the sleeve further comprising a wet wipe lining at least a portion of the inner surface of the sleeve.

2. A hygienic article for personal wear by a male, said hygienic article comprising an elongate fabric sleeve having a first end, a longitudinally opposite second end and a central passage extending longitudinally between the first and second ends of the sleeve, the first end of the sleeve being open to the central passage to permit the wearer's penis to extend through said open first end into the central passage of the sleeve with the first end of the sleeve nearer to the base of the wearer's penis than the second end of the sleeve, the second end of the sleeve also being open to the central passage, and a closure for the second end of the sleeve such that the sleeve is selectively configurable between a closed position in which the closure substantially closes the second end of the sleeve and an open position in which the second end of the sleeve is free from being blocked by the closure to permit the wearer to urinate through said open second end of the sleeve, the sleeve having a longitudinal direction extending longitudinally between the first and second ends of the sleeve and a transverse direction extending circumferentially about the sleeve, said sleeve being stretchable in the transverse direction of the sleeve for conforming the size and shape of the central passage of the sleeve to the wearer's penis.

3. The hygienic article set forth in claim 2 wherein the sleeve is at least in part constructed of an absorbent material.

4. The hygienic article set forth in claim 2 wherein the sleeve is stretchable in the longitudinal direction of the sleeve.

5. The hygienic article set forth in claim 4 wherein the sleeve is elastic in at least one of the longitudinal direction and the transverse direction of the sleeve.

6. The hygienic article set forth in claim 2 wherein the sleeve has a length sized such that the second end of the sleeve is disposed longitudinally outward beyond the tip of the wearer's penis during wear.

7. The hygienic article set forth in claim 2 wherein the sleeve has a length sized such that the wearer's penis extends outward beyond the second end of the sleeve during wear.

8. A hygienic article for personal wear by a male, said hygienic article comprising an elongate fabric sleeve having a first end, a longitudinally opposite second end and a central passage extending longitudinally between the first and second ends of the sleeve, the first end of the sleeve being open to the central passage to permit the wearer's penis to extend through said open first end into the central passage of the sleeve with the first end of the sleeve nearer to the base of the wearer's penis than the second end of the sleeve, the second end of the sleeve also being open to the central passage, and a closure for the second end of the sleeve such that the sleeve is selectively configurable between a closed position in which the closure substantially closes the second end of the sleeve and an open position in which the second end of the sleeve is free from being blocked by the closure to permit the wearer to urinate through said open second end of the sleeve, the sleeve having an inner surface defining the central passage of the sleeve, the sleeve further comprising a wet wipe lining at least a portion of the inner surface of the sleeve.

9. The hygienic article set forth in claim 2 wherein the sleeve has an inner surface defining the central passage of the sleeve, the sleeve further comprising a lubricious feature at the inner surface of the sleeve.

10. The hygienic article set forth in claim 2 wherein the sleeve has a length, said sleeve being constructed to permit selective adjustment of the length of the sleeve.

11. The hygienic article set forth in claim 2 wherein the closure comprises a fastening member secured to the sleeve at the second end thereof.

12. The hygienic article set forth in claim 11 wherein the fastening member comprises an adhesive strip.

13. The hygienic article set forth in claim 2 wherein the sleeve is elastic in the transverse direction of the sleeve for conforming the size and shape of the central passage of the sleeve to the wearer's penis.

* * * * *